US009480581B2

(12) United States Patent
Layman et al.

(10) Patent No.: US 9,480,581 B2
(45) Date of Patent: *Nov. 1, 2016

(54) METHOD OF DIGITALLY CONSTRUCTING A PROSTHESIS

(71) Applicants: William Stratford Layman, Kenner, LA (US); W. Brian Layman, Kenner, LA (US)

(72) Inventors: William Stratford Layman, Kenner, LA (US); W. Brian Layman, Kenner, LA (US)

(*) Notice: Subject to any disclaimer, the term of this patent is extended or adjusted under 35 U.S.C. 154(b) by 464 days.

This patent is subject to a terminal disclaimer.

(21) Appl. No.: 13/948,361

(22) Filed: Jul. 23, 2013

(65) Prior Publication Data

US 2014/0188260 A1   Jul. 3, 2014

Related U.S. Application Data

(60) Provisional application No. 61/674,720, filed on Jul. 23, 2012.

(51) Int. Cl.
*A61F 2/50*   (2006.01)

(52) U.S. Cl.
CPC ...... *A61F 2/5046* (2013.01); *A61F 2002/5049* (2013.01)

(58) Field of Classification Search
CPC ............... A61F 2/5046; A61F 2002/5049; A61F 2/60; A61F 2/66; A61F 2002/505
USPC ......... 700/98, 117, 182; 703/1, 6, 7; 623/27, 623/28, 53
See application file for complete search history.

(56) References Cited

U.S. PATENT DOCUMENTS

| 5,432,704 | A | * | 7/1995 | Vouzelaud | .......... B29C 67/0074 345/420 |
| 6,463,351 | B1 | | 10/2002 | Clynch | |
| 6,882,894 | B2 | * | 4/2005 | Durbin | ............... A61C 13/0013 433/213 |
| 7,033,400 | B2 | * | 4/2006 | Currier | ................. A61F 2/7812 425/2 |
| 7,162,322 | B2 | | 1/2007 | Arbogast et al. | |
| 7,225,050 | B2 | | 5/2007 | Sutula, Jr. | |
| 7,447,558 | B2 | | 11/2008 | Pratt | |
| 8,690,962 | B2 | * | 4/2014 | Dignam | ................ A61F 2/5046 623/33 |
| 8,978,224 | B2 | * | 3/2015 | Hurley | ...................... A61F 2/80 29/407.1 |
| 2004/0260402 | A1 | * | 12/2004 | Baldini | ................. A61F 2/5046 623/33 |

(Continued)

*Primary Examiner* — Charles Kasenge
(74) *Attorney, Agent, or Firm* — Garvey, Smith, Nehrbass & North, L.L.C.; Gregory C. Smith; Julia M. FitzPatrick

(57) ABSTRACT

A prosthetic limb and process to digitally construct a prosthetic limb which includes first, digitally producing a modified mold of a residual limb via 3d scanners and software; constructing a test socket from the digitally modified mold and be equipped with an alignable system; accurately scanning the test socket, along with finalized alignment that has been recorded and adjusted by a certified practitioner to provide a 3-D Image of the finalized prosthetic alignment; transferring the finalized digital alignment of the test socket to the finalized digitally modified mold; once the modified model has received the transferred alignment, fabricating the type of hookup in the socket; i.e., plug fit, four hole, support drop lock, or any other type of industry standard connection or accommodation via basic 3D software; and once the desired prosthetic attachment is finalized, sending finished file to a 3-D printer to produce the definitive prosthetic device.

14 Claims, 8 Drawing Sheets

(56) References Cited

U.S. PATENT DOCUMENTS

| | | |
|---|---|---|
| 2006/0020348 A1 | 1/2006 | Slemker et al. |
| 2006/0094951 A1 | 5/2006 | Dean et al. |
| 2007/0225795 A1* | 9/2007 | Granada .................. A61F 2/91 623/1.15 |
| 2010/0023149 A1 | 1/2010 | Sanders et al. |
| 2010/0161076 A1 | 6/2010 | Pallari |
| 2010/0268138 A1* | 10/2010 | Summit .................. A61F 5/013 602/16 |
| 2012/0179272 A1* | 7/2012 | Dignam ................ A61F 2/5046 623/33 |
| 2013/0123940 A1* | 5/2013 | Hurley ...................... A61F 2/80 623/33 |
| 2013/0164960 A1* | 6/2013 | Swanson ............ B29C 67/0055 439/199 |

* cited by examiner

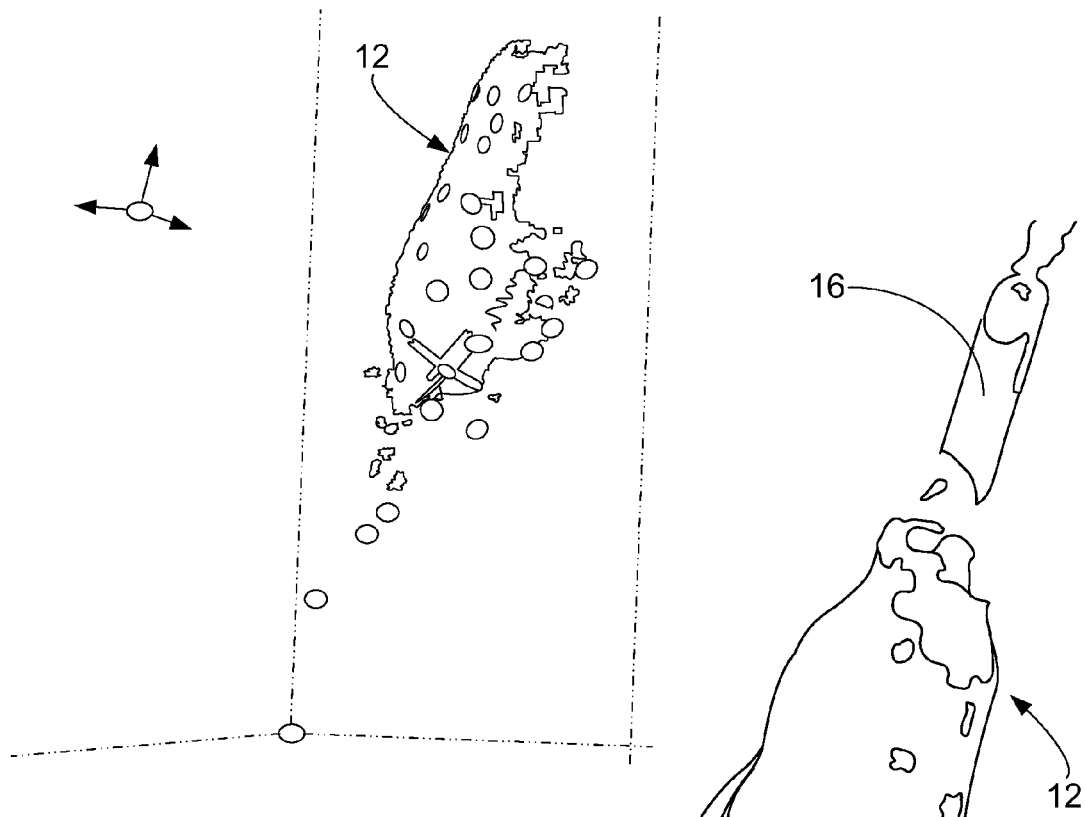
FIG. 4A
FIG. 4B
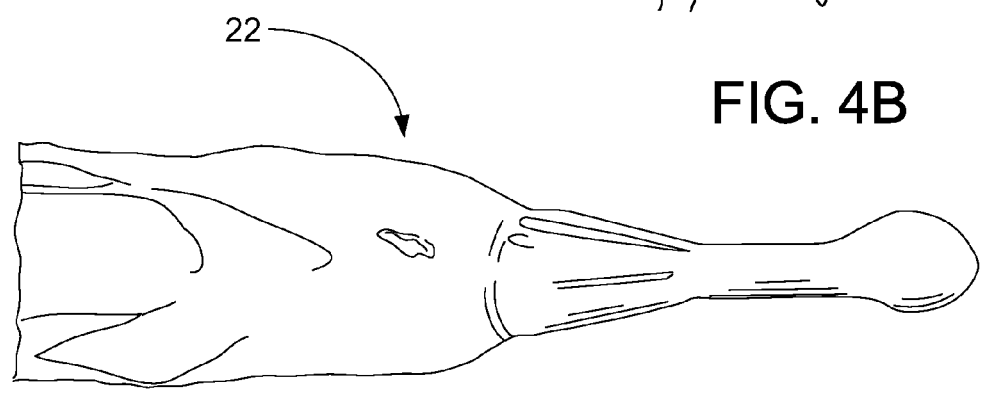
FIG. 4C

METHOD OF DIGITALLY CONSTRUCTING A PROSTHESIS

CROSS-REFERENCE TO RELATED APPLICATIONS

This is a nonprovisional patent application of U.S. Provisional Patent Application Ser. No. 61/674,720, filed Jul. 23, 2012, which is hereby incorporated herein by reference.

Priority of U.S. Provisional Patent Application Ser. No. 61/674,720, filed Jul. 23, 2012, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to prosthetics. More particularly, the present invention relates to a novel process for constructing a prosthetic limb through a series of fabrication steps including retrieving a file from a computer, manipulating that file that has captured alignment and socket fit, sending it to a 3D printer, which in turn has the ability to print out a completed, wearable prosthetic limb of strong plastic material, such as ULTEM® (A Registered Trademark of General Electric Co.), carbon fiber, or other material of equivalent or greater strength that may be known or developed in the future.

2. General Background of the Invention

The design of an effective prosthetic socket is crucial to the rehabilitation and overall health of a person with an amputated limb. Most of the time and energy a practitioner applies in making a prosthesis is spent on fabricating the socket that must be fitted to the residual limb. The prosthetic socket must be shaped so that it supports the residual limb in load tolerant areas, while avoiding irritation of sensitive regions on the limb that contact the inner surface of the socket. If these criteria are not achieved, when the patient uses the prosthesis, residual limb soft tissue breakdown often occurs. The result is painful sores, blisters, ulcers, or cysts on the residual limb that typically restrict continued prosthesis use, and in severe cases, necessitate a further amputation to a higher anatomical level, which can lead to further disability. The incidence of skin breakdown in lower-limb amputees has been reported to be from 24% to 41%. Accordingly, at any one time, as many as 41% of prosthesis users may be experiencing breakdown of the tissue on the residual limb. The principal cause of such breakdown is a poorly fitting prosthetic socket.

Practitioners face challenges in making quality sockets for the increasing amputee popularity. Also, there is a shortage of prosthetists in the industry, and that shortage is expected to increase in the future, as the demand for prosthetic devices increases. A prosthetist's time is precious and must be used as efficiently as possible. It will therefore be evident that there is a need for technology to improve a prosthetist's efficiency, speed, documentation, repeatability, and quality of fitting a socket to a patient's residual limb, and to ensure a proper socket design early in the process of fitting a prosthetic socket to a recipient.

In the current state of the art, one way of capturing an image of a residual limb in order to gather a positive mold is by hand casting. The procedure one would use in the traditional format of hand casting would follow certain steps. The initial step would include the following materials and tools needed for measuring the patient: stockinette, plaster bandages, indelible pencil, preparations for suspension (example: silicone liners, foam liners, hard socket), also measuring tools such as a length stick M/L gauge and tape measure. These tools and materials would assist a prosthetist in taking the proper cast along with techniques they acquired through training.

After the proper cast has been taken by a certified individual, the fabrication of the test socket would be as follows. First, one would pour the negative mold or cast in order to receive the positive mold with a powder substance called plaster of paris. Once the plaster hardens, the next step is striping the plaster bandages off of the mold. Then the positive mold is modified by hand to achieve its voids and pressure points in precise locations with plaster of paris. After the desired reliefs are added it is then ready for a term used in the industry known as either drap pull or bubble pull. These are techniques in which a clear plastic is pulled over the positive model. Therefore, this manual technique for capturing an image of a residual limb in order to gather a positive mold is greatly improved upon by the use of a digital process as will be described herein.

The following U.S. patents are incorporated herein by reference:

| Patent No. | Title | Issue Date |
| --- | --- | --- |
| 7,447,558 | Apparatus for Determining A Three Dimensional Shape of an Object | Nov. 4, 2008 |
| 7,225,050 | Method and Apparatus for Precisely Fitting, Reproducing, and Creating 3-Dimensional Objects from Digitized and/or Parametric Data Inputs Using Computer Aided Design and Manufacturing Technology | May 29, 2007 |
| 7,162,322 | Custom Prosthetic Liner Manufacturing System and Method | Jan. 9, 2007 |
| 6,463,351 | Method for Producing Custom Fitted Medical Devices | Oct. 8, 2002 |
| 2010/0161076 | Orthotic or Prosthetic Cushioned Device and Method of Making the Same | Jun. 24, 2010 |
| 2010/0023149 | Computer Aided Design and Manufacturing of Transtibial Prosthetic Sockets | Jan. 28, 2010 |
| 2006/0020348 | Method and Associated System for Recording and Retrieving Fabrication and/or Fitting Data Associated with a Prosthetic Component | Jan. 26, 2006 |
| 2006/0094951 | Computer-Aided-Design of Skeletal Implants | May 4, 2006 |

BRIEF SUMMARY OF THE INVENTION

The method and process of the present invention solves the problems confronted in the art in a simple and straightforward manner. What is provided is a process for making a prosthetic limb, wherein one would retrieve a manipulated file from a computer that has been through the test socket phase; that file will be manipulated through the definitive socket phase using specific 3D prosthetic software to design the socket for current practiced methods. Thereafter it will be ready to be sent to a 3D printer, which in turn has the ability to print out the prosthetic limb from a material, such as a strong plastic material, ULTEM®, or carbon fiber, or other material of equivalent or greater strength that may be known or developed in the future.

More specifically, the steps in this inventive process include, first, digitally producing a modified mold of a residual limb via 3D scanners and software known to the industry. A test socket would be constructed from the digitally modified mold and be equipped with an alignable system; for example, a pylon, along with the desired prosthetic foot. The test socket would be accurately scanned, preferably with a 3D scanner, along with finalized alignment that has been recorded and adjusted by a certified practitioner to provide a 3-D Image of the finalized prosthetic alignment. The next step would be to transfer the finalized digital alignment of the test socket to the finalized digitally modified mold. Once the modified model has received the transferred alignment, one would proceed to fabricate the type of hookup in the socket; i.e., plug fit, four hole, support drop lock, or any other type of industry standard connection or accommodation via basic 3D software. Once the desired prosthetic attachment is finalized, the next step is to send the finished file to a 3-D printer to produce the definitive prosthetic device. One such printer is sold under the trademark of Fortus® which would be utilized in this process designed by Stratasys, but there may be other such printers available. Preferably, the prosthesis would be printed out of a material such as ULTEM®, or carbon fiber, or other material of equivalent or greater strength that may be known or developed in the future.

As stated earlier, by utilizing this process, the prosthetist is allowed to construct the prosthesis with prosthetic techniques for attachments such as:

Four hole hook up with vacuum
Four hole hook up that will support a drop lock
Fitting of pylon or adapters
Custom attachments (for certain feet/attachment)

Therefore, it is a principal object of the present invention to provide a prosthesis and a method to fabricate a prosthesis constructed of a plastic material such as ULTEM®, or carbon fiber, or other material of equivalent or greater strength that may be known or developed in the future, through the use of digital manipulation of a file that has captured the alignment and the socket measurements, then created a definitive prosthesis by a method which can be done in an efficient rate and manner than the conventional methods which are time consuming.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIGS. 4A through 4B illustrate steps in the scanning of the test socket and the alignment, with FIG. 4C illustrating the captured alignment;

DETAILED DESCRIPTION OF THE INVENTION

Figure 1:
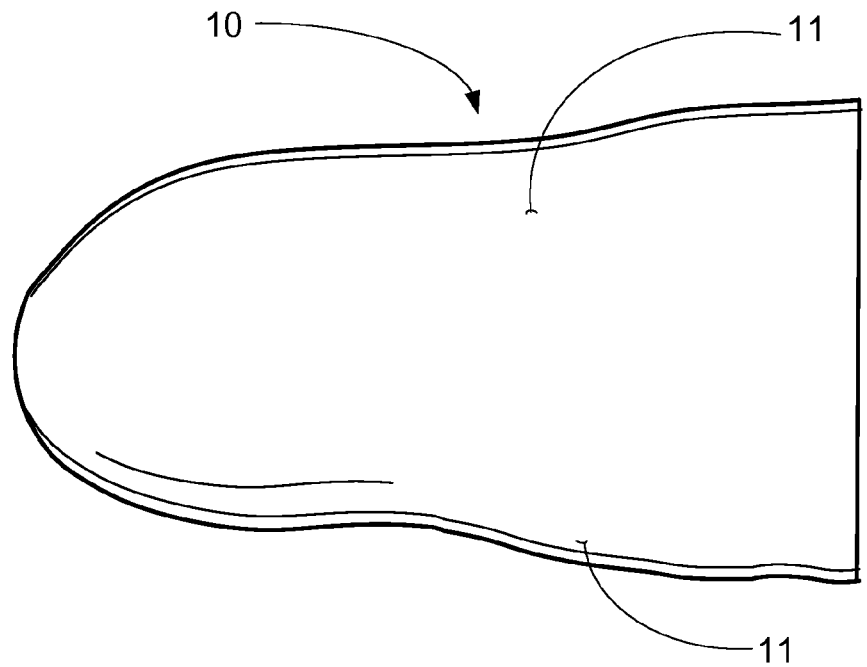
FIG. 1 illustrates a modified mold of a residual limb digitally produced via 3D scanners and software.

FIGS. 1 through 12 illustrate a preferred embodiment of the method or process of constructing a prosthetic limb through a digital format.

Before reference is made to the Figures, in general, this technique of achieving a positive mold for a test socket in a digital format is by scanning the residual limb. The first step would be to choose the materials and tools needed for measuring a patient. Again, one would need to prepare suspension of the prosthesis (silicone liner, foam or other types of socket designs); a scanner; a laptop; reflective dots; measuring tools such as a length stick M/L gauge tape measure, etc. The method may vary by which Distal Device used.

After preparing oneself with the items one would need to take a digital image of a residual limb, the individual would use a scanner to capture the digital image of the limb. After the limb is captured, the individual would use a prosthetic software which is already known in the art, to modify the 3-D image or positive mold to achieve its relief and pressure points in precise locations. In essence one would modify the residual limb with the same basic techniques that are taught and used in the pre-scanner era or plastic molds.

After modifying the mold in the desired manner via CAD, the positive mold is designed, and the final stages of a test socket is near. Before one would vacuum pull a test socket, a trained individual would determine the proper plastic material, and certain mechanical attachments were needed. Also required is the technique discussed earlier of forming the plastic over the mold (drape or bubble pull). Finally, after the plastic has cooled to a workable form, one would clean the proper trim lines, make final mechanical preparations and finalize the test socket before fitting the patient.

During the fitting of the test socket, one would observe pressure points and proper fit of the test socket. Next, one would make adjustments if needed and fabricate a second socket if need be. At this time, alignment can be observed and obtained.

When the fabrication of the definitive sockets materials have cured, the socket is removed from the mold and trimmed out. It is then applied to the desired prosthetic components in the final delivery, i.e., during the fit/walk, the prosthetist is looking for the proper fit of socket and the correct alignment that correspond to the patient's gait.

In the process of the present invention, the individual would receive the aligned test socket, then one would capture the alignment and achieve a digital alignment via scanners and CAD systems along with the final test socket, the images can be merged to create a positive mold in an alignment.

Once the digital prosthetic design is complete and approved, it is then sent to a 3-D printer where it is then printed or fabricated as a wearable prosthetic limb. As stated earlier, one such printer is sold under the trademark of Fortus® which would be utilized in this process designed by Stratasys, although there may be other such printers available for use.

During this process the preferred material may be a plastic, such as ULTEM®, or carbon fiber, or other material of equivalent or greater strength that may be known or developed in the future, while the printers are a product of Stratasys Corporation or other such types of printers. After the print is complete, the prosthetic limb is then shipped to the prosthetist. Upon delivery, the prosthetist will have an aligned prosthesis and would have the ability to finish the proper trim lines. During fit/walk the prosthetist is looking for the proper fit of socket and the correct alignment that corresponds to the patient's gait.

Figure 2:
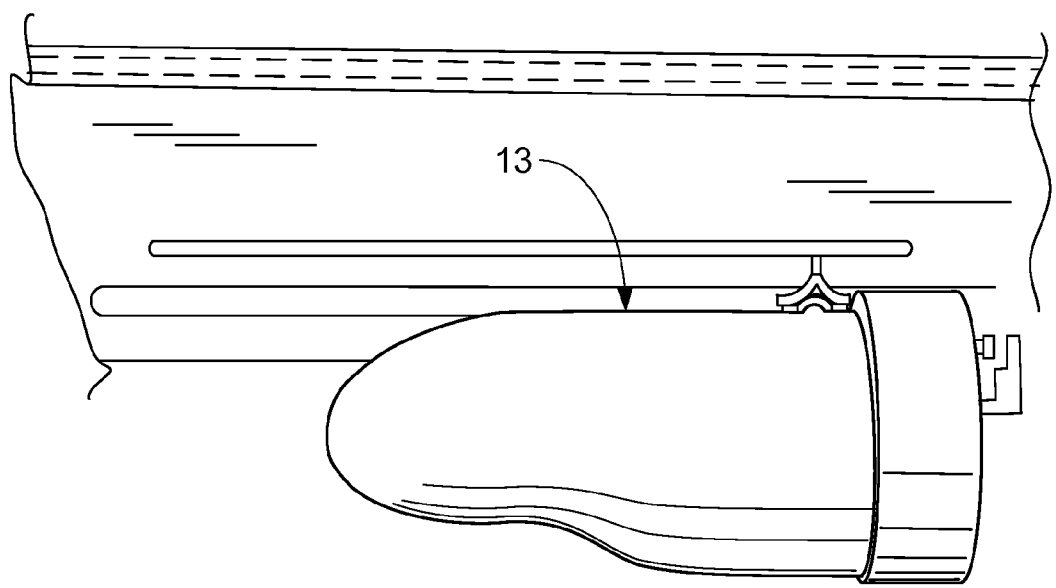
FIG. 2 illustrates a carving of the modified model before it goes with the test socket to be fabricated.
Figures 3A, 3B:
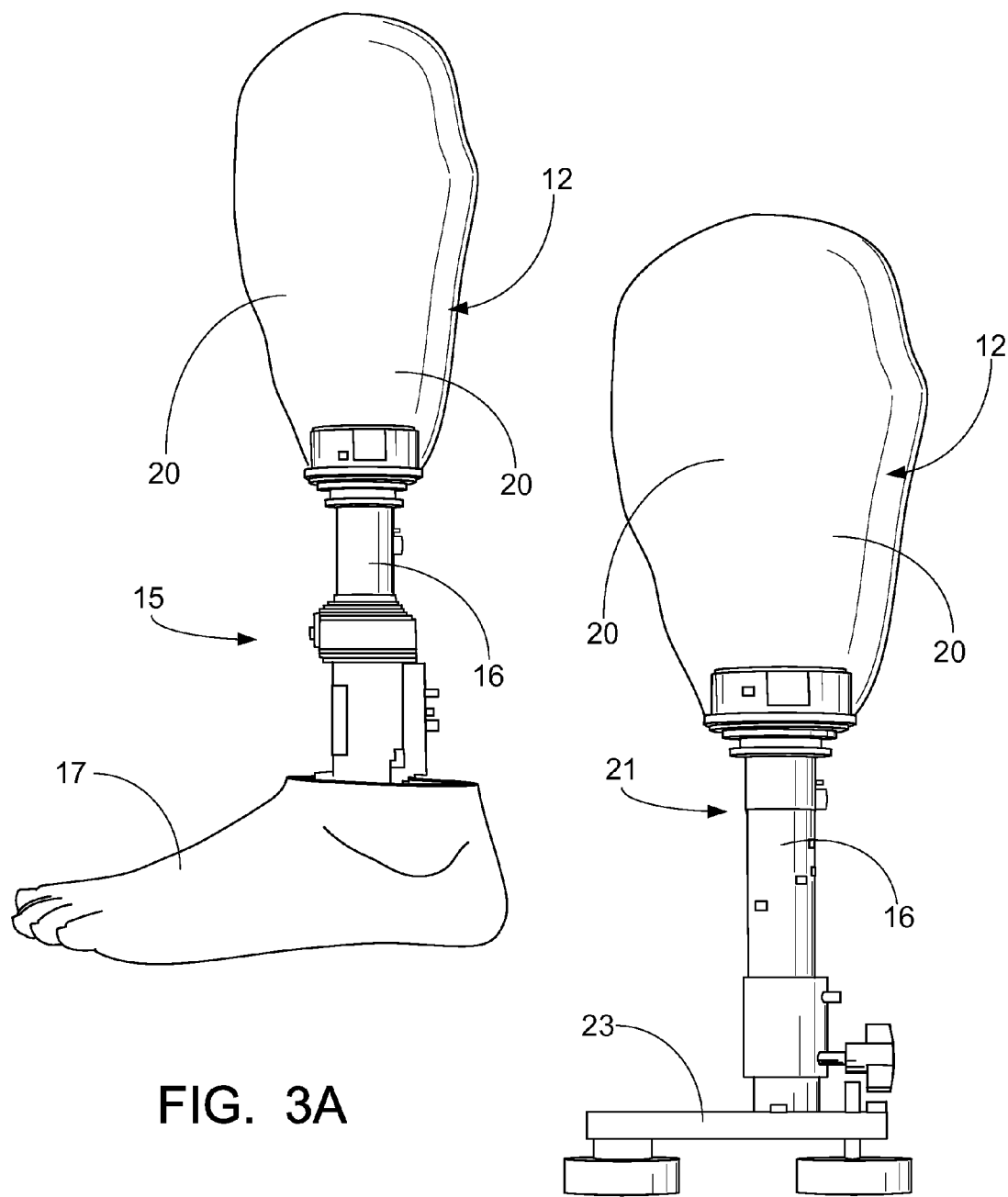
FIGS. 3A and 3B illustrate two views of a fabricated test socket which is hooked up to an alignment or an alignable system respectively.

Turning now to FIGS. 1 through 11, there is illustrated the various steps involved in the method of the present invention. In FIG. 1 there is illustrated a modified mold 10 of a residual limb which has been digitally produced via 3D scanners and software known in the industry. As illustrated, the modified mold 10 would include the relief and pressure points 11 of a test socket which would be actually molded. In FIG. 2, there is illustrated a carving 13 of a modified model before it is matched with the test socket to be fabricated. Turning to FIG. 3A there is illustrated an actual test socket 12 which has been constructed from the digitally modified mold 10, which is hooked up to an alignment system 15, having a pylon 16 and a prosthetic foot 17. In FIG. 3B, the test socket 12 has been equipped with an alignable system 21, including a pylon 16, together with base 23 of the alignable system 21, rather than the prosthetic foot 17 as seen in FIG. 3A. It should be noted that the actual test socket 12, as seen in FIGS. 3A and 3B, has also been equipped with a plurality of dots 20 so as to allow the socket 12 to be accurately scanned, as covered by the next step in the process.

FIGS. 4A and 4B illustrate the images which appear of the test socket 12 as the test socket 12 is being accurately scanned. preferably with a 3D scanner, along with finalized alignment that has been recorded and adjusted by a certified practitioner to provide a 3-D Image of the finalized captured prosthetic alignment, or the completed image of the aligned prosthetic limb 22 which is illustrated in FIG. 4C.

Figure 5A:
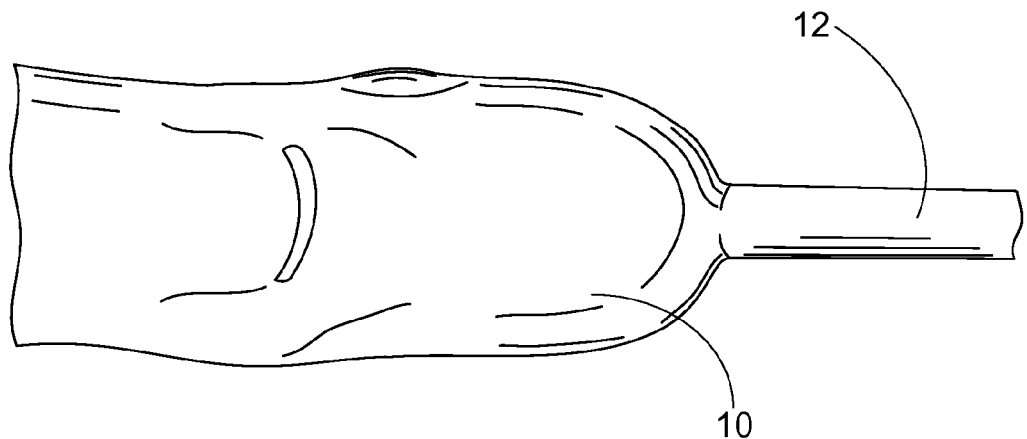
FIGS. 5A and 5B illustrate the modified mold and the beginning stages of transferring alignment, illustrating the addition of the pylon.
Figure 5B:
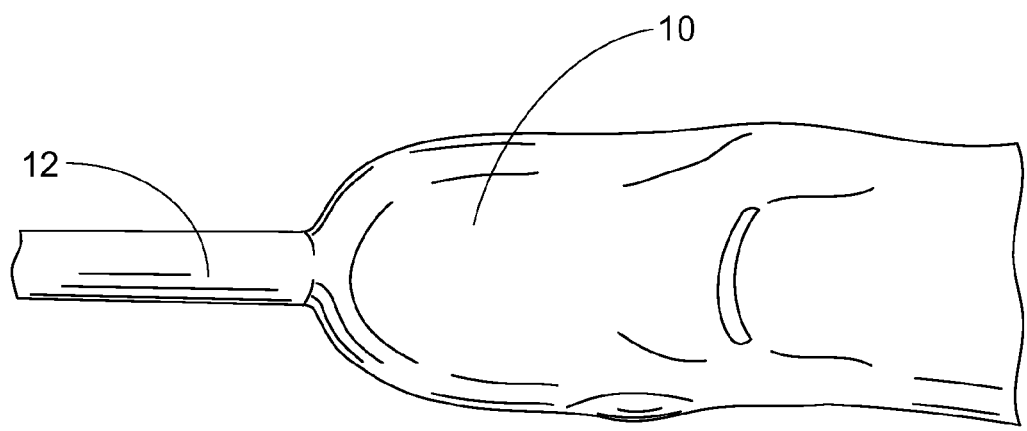
Figures 6, 7:
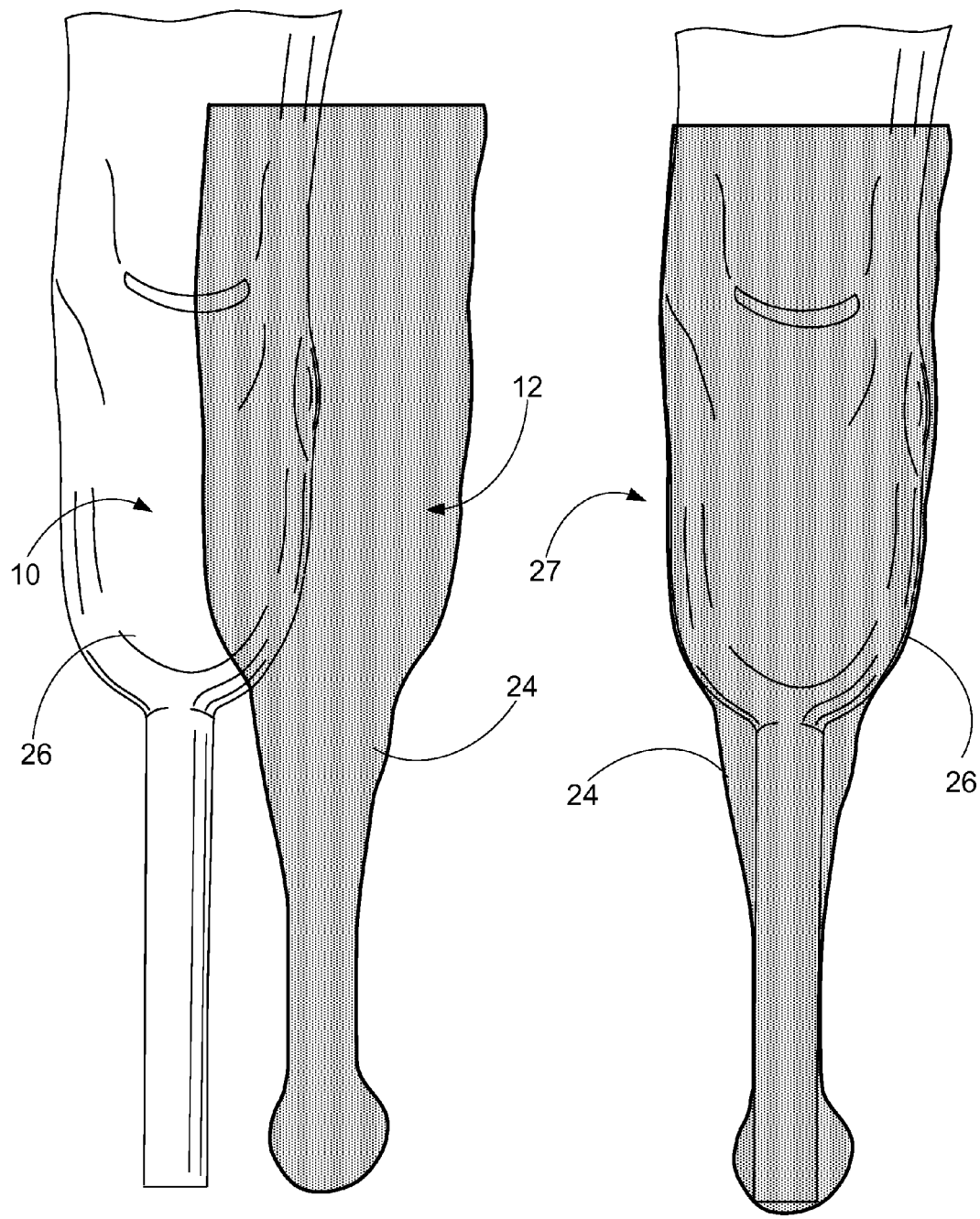
FIG. 6 illustrates the process of cross-referencing of the modified mold with the alignment attachment with the test socket with the correct alignment.
FIG. 7 is the completed merge of the process illustrated in FIG. 6 to assure the correct alignment.

In FIGS. 5A and 5B there is illustrated examples of the modified mold and the beginning stages of transferring the alignment. It should be noted that in FIG. 5A, there has been placed a 30 mm adaption (pylon 16), while in FIG. 5B there is a shorter adaption (pylon 16) adapted to the modified mold. The next step would be to transfer the finalized digital alignment of the test socket 12 to the finalized digitally modified mold 10, as is illustrated in FIG. 6. In FIG. 6, the image on the left is the modified mold 10 with the alignment attachment that can be manipulated, on the right is the test socket 12 with the correct alignment. In this step, one is merging the alignment of a test socket (inner portion 24 of a prosthesis) with the final manipulated model (outer fit 26 of the prosthesis) as one. This is done by using techniques in the software that allows one to overlap the images to cross reference the objects at hand. But first using a certain cylindrical tool in the software to simulate the appearance of a pylon 16 (normally 30 mm) needs to be added to the distal portion of the final manipulated model (inner model). This will give the individual the option of lining up the alignment or changing it at this time. When cross-referenced, both models should line up exactly using the alignment model as reference. In FIG. 7, there is illustrated the final merged image 27 of both to assure there is correct alignment which does not have to be modified or corrected. In the process described above, it is foreseen that in the future this process as described herein will be accomplished through software to be developed.

Figure 8:
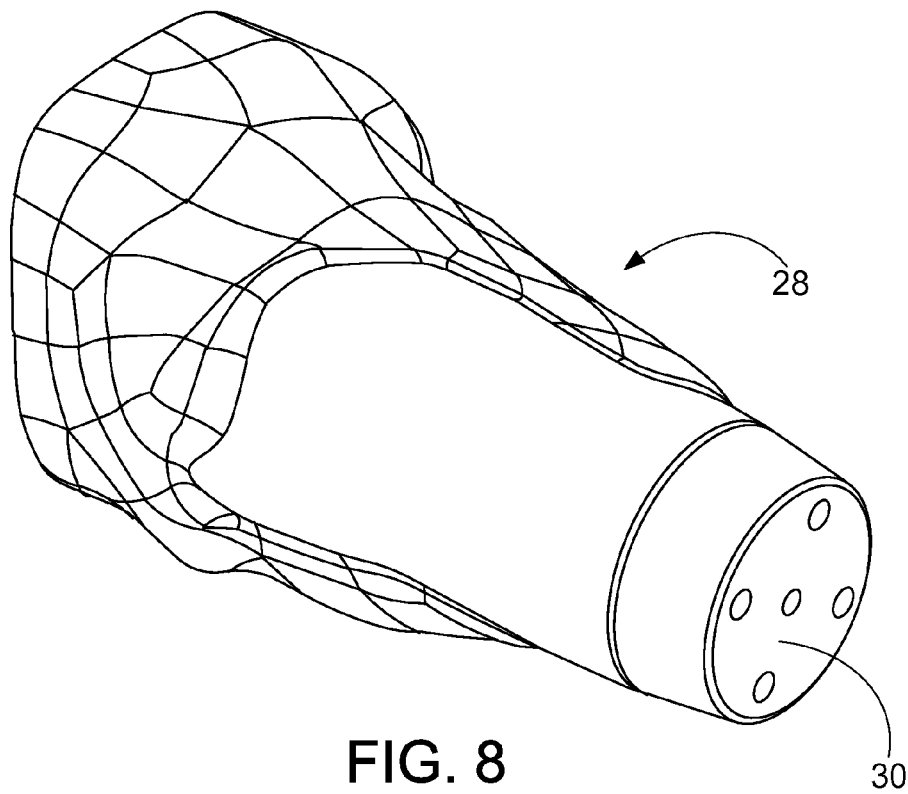
FIG. 8 is an image of the socket after alignment has been captured and with the use of CAD software showing a four hole hookup adapted to the socket.
Figure 9:
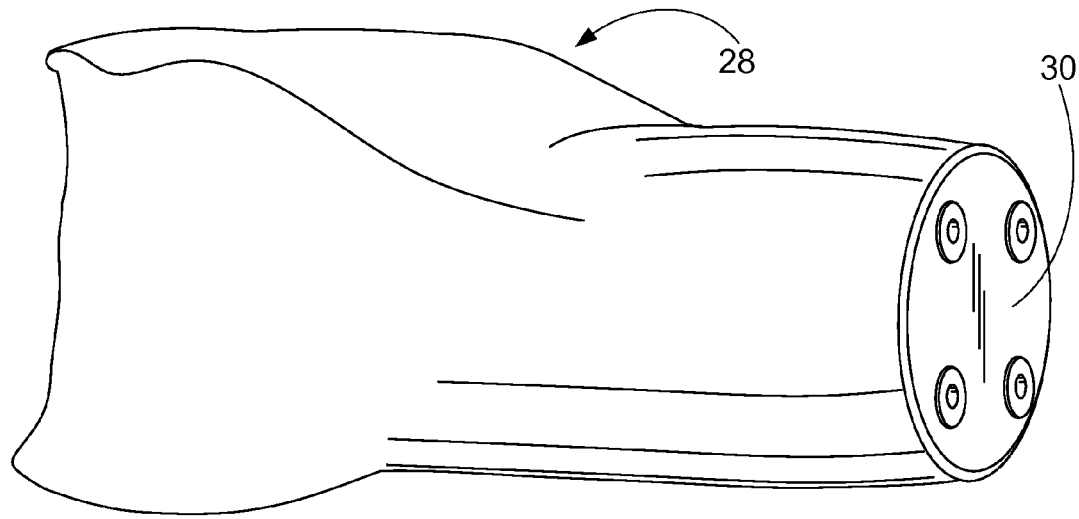
FIG. 9 is an actual printout of the image in FIG. 8 showing the four hole hookup.

In FIG. 8, after the alignment has been captured, as described above, the next step is to use CAD software to proceed to fabricate the type of hookup in the definitive socket 28; i.e., plug fit, four hole (the type illustrated in FIG. 8), support drop lock, or any other type of industry standard connection or accommodation via basic 3D software. In FIG. 9, there is illustrated the actual printout of the prosthesis, also referred to as definitive socket 28, that was illustrated in FIG. 8, showing the four hole hookup 30 mounted on the definitive prosthetic socket 28. One such printer is sold under the trademark of Fortus® which would be utilized in this process designed by Stratasys, although other such printers are available. Preferably, the definitive socket 28 prosthesis would be printed out of a plastic material such as ULTEM®, or carbon fiber, or other material of equivalent or greater strength that may be known or developed in the future.

Figures 10, 11:
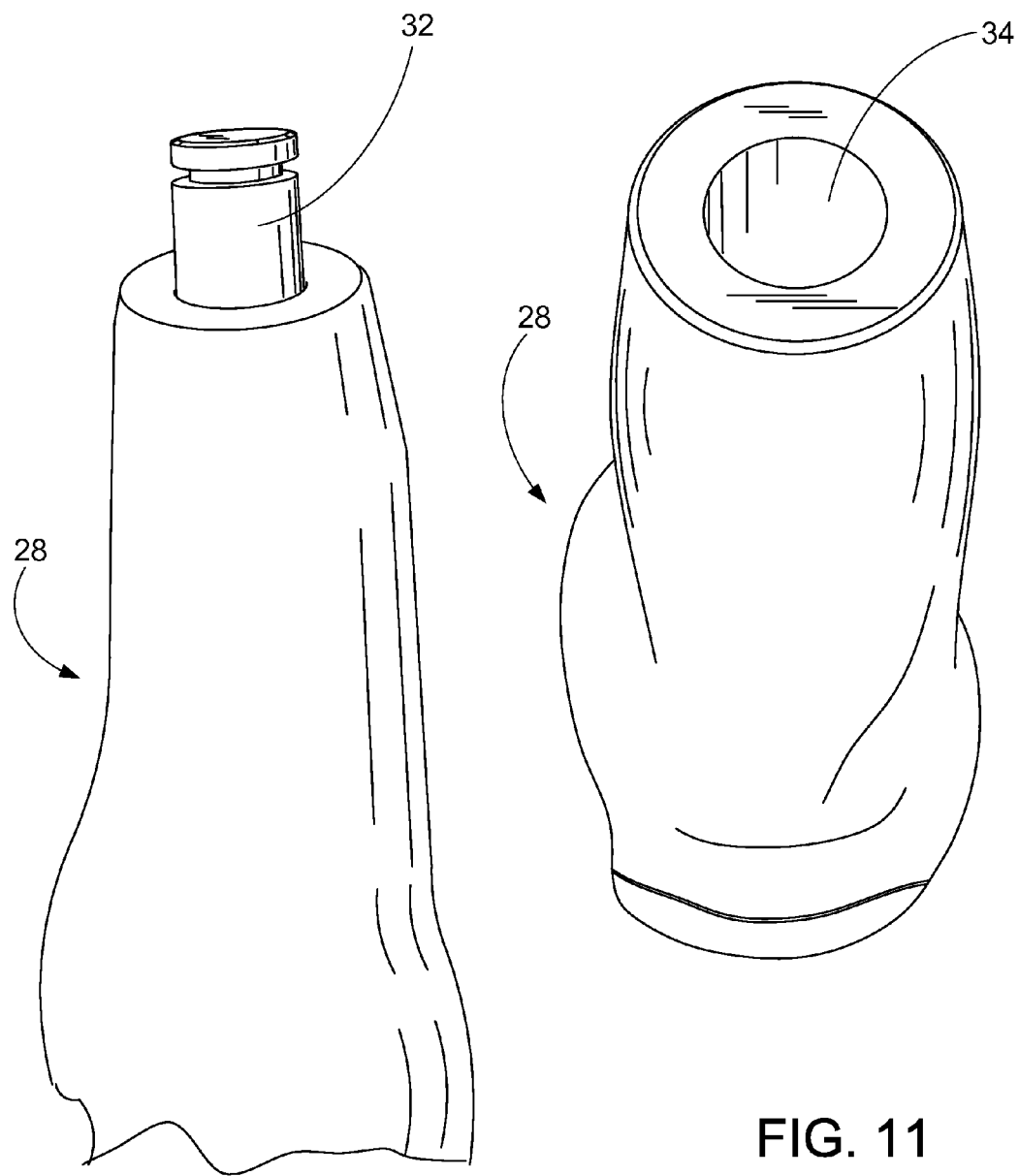
FIG. 10 is a printout of the prosthesis which has a plug fit adaptor.
FIG. 11 is a printout of the prosthesis which has a plug fit where a pylon or adaptor can be engaged.
Figure 12:
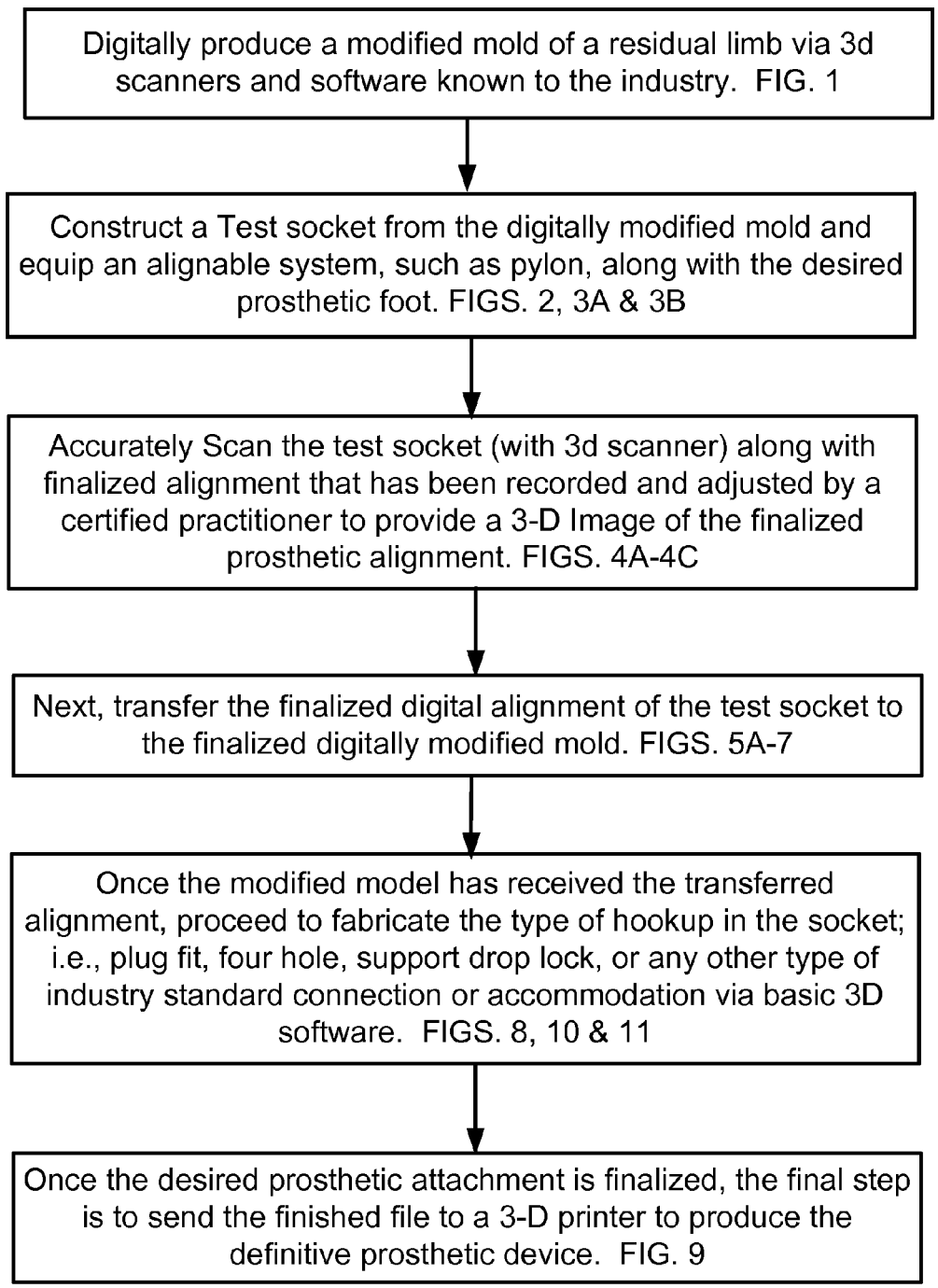
FIG. 12 is a Flow Chart illustrating a preferred embodiment of the method or process of constructing a prosthetic limb through a digital format.

In addition to the four hole hookup 30 as illustrated in FIG. 9, FIG. 10 illustrates a printout of the prosthesis 28 which has a plug fit adaptor 32, while in FIG. 11 the prosthesis 28 is adapted with a plug fit 34 for receiving a pylon 16 or other type of adaptor.

As stated earlier, by utilizing this process, the prosthetist is allowed to construct the prosthesis with prosthetic techniques for attachments such as:

Four hole hook up with vacuum
Four hole hook up that will support a drop lock
Fitting of pylon or adapters
Custom attachments (for certain feet/attachment)

In the preferred method of the present invention it is foreseen that the socket will undergo sealing. In order to seal the socket the step will include adding a layer of epoxy to the exterior of the socket, which would help to add strength to the entire socket. The preferred type of epoxy is described as TC-1614 A/B epoxy, manufactured by BJB Enterprises, or an equivalent type, which will be laminated over the socket. This will seal the socket in order to be able to use vacuum for proper fitting, if required.

In addition to the Drawing Figures as discussed above, reference is made to FIG. 12, a Flow Chart which succinctly depicts the steps in the process of the present invention making reference to the appropriated drawing Figures as discussed herein.

All measurements disclosed herein are at standard temperature and pressure, at sea level on Earth, unless indicated otherwise. All materials used or intended to be used in a human being are biocompatible, unless indicated otherwise.

| PARTS LIST | |
|---|---|
| Modified mold | 10 |
| Pressure points | 11 |
| Test socket | 12 |

-continued

| PARTS LIST | |
|---|---|
| Carving | 13 |
| Alignment system | 15 |
| Pylon | 16 |
| Prosthetic foot | 17 |
| Dots | 20 |
| Alignable system | 21 |
| Aligned prosthetic limb | 22 |
| Base | 23 |
| Inner portion | 24 |
| Outer fit | 26 |
| Merged image | 27 |
| Definitive socket | 28 |
| Four hole hookup | 30 |
| Plug Fit Adaptor | 32 |
| Plug fit | 34 |

The foregoing embodiments are presented by way of example only; the scope of the present invention is to be limited only by the following claims.

The invention claimed is:

1. A process to digitally construct a prosthetic limb, comprising the following steps:
   a) digitally producing a modified mold of a residual limb via 3D scanners and software;
   b) constructing a test socket from the digitally modified mold of the residual limb;
   c) equipping the test socket with an alignable system, including a pylon, along with a base member;
   d) aligning the test socket equipped with the alignable system and determining a finalized prosthetic alignment of the test socket;
   e) scanning the test socket in the finalized prosthetic alignment to provide an image of the finalized prosthetic alignment; and
   f) transferring the finalized prosthetic alignment of the test socket to a finalized digitally modified mold of an aligned socket.

2. The process in claim 1, wherein the test socket in the finalized prosthetic alignment is scanned with a 3D scanner.

3. The process in claim 1, further comprising after step "f" fabricating a hookup in the finalized digitally modified mold of the aligned socket, the hookup for a prosthetic attachment, via software.

4. The process in claim 3, further comprising creating a finished file once the hookup for the prosthetic attachment is fabricated and sending the finished file to a printer to produce the aligned socket with the hookup.

5. The process in claim 4, wherein the printer is a 3-D Fortus® printer.

6. The process in claim 2, wherein the prosthetic limb is printed out of a plastic material.

7. The process in claim 1, further comprising fabricating an attachment in the finalized digitally modified mold of the aligned socket, via software, the attachment selected from a group comprising:
   a) a four hole hook up with vacuum;
   b) a four hole hook up that will support a drop lock;
   c) a fitting of cylindrical adapter; and
   d) a custom attachment for receiving a foot or other attachment member.

8. The process in claim 1 wherein the base member is a prosthetic foot.

9. The process in claim 2 wherein the prosthetic limb is printed out of carbon fiber.

10. The process in claim 3 wherein the hookup is a plug fit, a four hole fit, or a support drop lock.

11. The process in claim 4 wherein the prosthetic limb is in alignment and wearable by a patient after being printed.

12. The process in claim 6 wherein the material is ULTEM® plastic.

13. The process in claim 1 wherein in step "f" the finalized prosthetic alignment is for an inner portion of the prosthetic limb, and the finalized digitally modified mold is for an outer portion of the prosthetic limb, and wherein when transferring the finalized prosthetic alignment of the test socket to the finalized digitally modified mold the finalized prosthetic alignment of the test socket is merged with the finalized digitally modified mold.

14. A digitally fabricated prosthetic limb, wherein a finished limb is aligned and capable of being worn by a patient, the digitally fabricated prosthetic limb fabricated under the following process:
   a) digitally producing a modified mold of a residual limb via 3d scanners and software;
   b) constructing a test socket from the digitally modified mold;
   c) equipping the test socket with an alignable system, including a pylon, along with a prosthetic foot;
   d) aligning the test socket with the alignable system and recording a finalized prosthetic alignment;
   e) accurately scanning the test socket, along with the finalized prosthetic alignment, to provide a 3-D image of the finalized prosthetic alignment; and
   f) using software to transfer the finalized prosthetic alignment of the test socket to a finalized digitally modified mold of an aligned socket.

* * * * *